United States Patent [19]

Manska et al.

[11] Patent Number: 4,823,167
[45] Date of Patent: Apr. 18, 1989

[54] CATHETER CALIBRATION DEVICE

[75] Inventors: Wayne E. Manska, Anaheim; Roger G. Bickelhaupt, Modjeska Canyon, both of Calif.

[73] Assignee: Baxter International Inc., Deerfield, Ill.

[21] Appl. No.: 942,356

[22] Filed: Dec. 16, 1986

[51] Int. Cl.$^4$ ............................................. G02B 23/24
[52] U.S. Cl. ................................... 356/243; 128/634; 206/364; 206/571
[58] Field of Search .................. 356/42, 243; 206/364, 206/57; 128/634

[56] References Cited

U.S. PATENT DOCUMENTS 4,050,450  9/1977  Polanyi et al. .................. 356/243 X
4,322,164  3/1982  Shaw et al. ........................ 356/243
4,650,327  3/1987  Ogi ..................................... 356/243

OTHER PUBLICATIONS

Conrad et al., "Spectrophotometer Calibrator" *IBM Tech. Disclos. Bull.*, vol. 20, No. 12, pp. 5239-5240.

Primary Examiner—Davis L. Willis
Assistant Examiner—Matthew W. Koren
Attorney, Agent, or Firm—Debra E. Dahl; Gordon L. Peterson

[57] ABSTRACT

A calibration device to be used in calibrating a separate catheter of the type having a catheter tube through which light can be propagated to an end portion of the catheter tube, includes a calibration element defining a cavity extending along a cavity axis to an open end that has a size and shape adapted to receive the end portion of the catheter tube for calibration purposes. A body of resiliently deformable material with which to hold the catheter tube and thereby retain the end portion within the cavity is retained in generally fixed proximity with the open end of the cavity by a retainer member, and a channel-defining portion of the body of resiliently deformable material defines a longitudinally-opening channel generally aligned with the cavity axis that has a size and shape adapted to receive the catheter tube in an interference fit. The channel receives the catheter tube by movement of the catheter tube into the channel radially after the end portion of the catheter tube has been placed into the cavity, and it inhibits movement of the catheter tube axially to thereby inhibit movement of the end portion within the cavity.

26 Claims, 2 Drawing Sheets

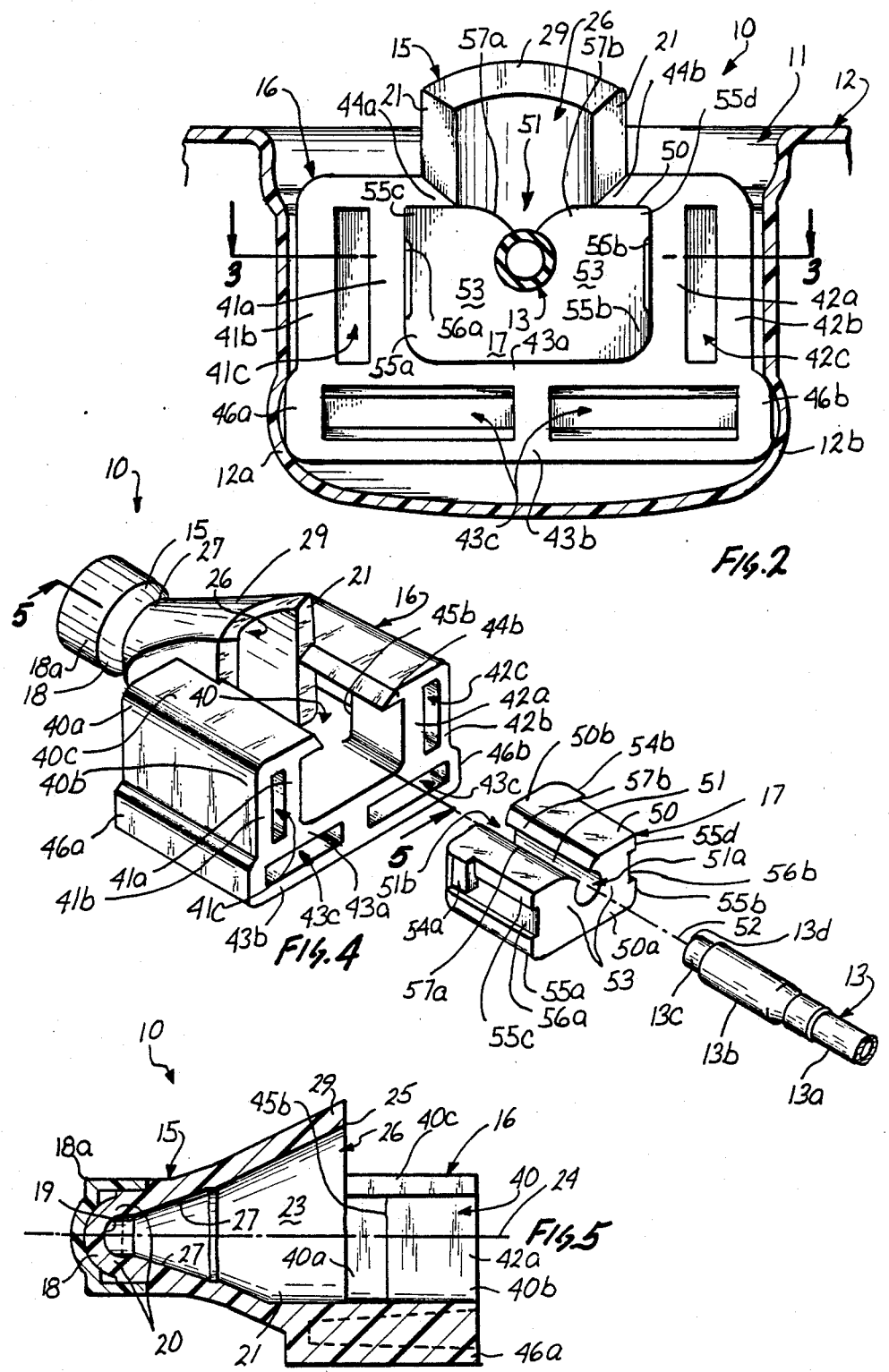

CATHETER CALIBRATION DEVICE

BACKGROUND OF THE INVENTION

1. Technical Field

This invention relates generally to optical catheter calibration, and more particularly to a catheter calibration device featuring a new and improved retainer arrangement for retaining the catheter in proximity with the calibration element.

2. Background Information

Calibration of an optical catheter, which may or may not also include calibration of the associated instrumentation, is often accomplished with a calibration element of known optical properties placed over the end portion of the catheter tube. Light propagated through the catheter tube returns from the calibration element to suitable instrumentation, with the measurements taken providing an optical characterization of the chatheter and instrumentaion. This characterization is then used to quantify subsequent measurements taken of a sample under examination.

In calibrating the catheter, it is important that the end portion of the catheter tube be retained in a preferred proximity with the calibration element, and that this be done in a sterile environment while enabling a convenient, repeatable calibration prior to catheter use. However, existing devices intended to accomplish this have certain drawbacks that need to be overcome.

For example, U.S. Pat. No. 4,322,164 to Shaw et al. describes a box that is sealed with the catheter in a dual-envelope sterilizable package so that the end portion of the catheter is located loosely in the box. In order to calibrate the catheter, the box is actuated by pressing a trigger mechanism through the package wrapper, and this causes a resilient holder to grip the catheter tube as a spring drives a calibration element in the form of a reflective calibrant material against the catheter tip.

Thus, the end portion of the catheter is placed and retained against the calibration element for calibration purposes, but only with a relatively complicated and expensive mechanical device. Therefore, it is desirable to have a new and improved arrangement for doing this—a calibration device that is less complicated and less expensive that achieves the desired function of catheter tube retention proximate the calibration element in a sterile environment enabling convenient, repeatable catheter calibration.

SUMMARY OF THE INVENTION

This invention recognizes the problems associated with the prior art and provides a new and improved catheter calibration device with the desired attributes.

Briefly, the above and further objects of the present invention are realized by providing a calibration device that includes a clamp member retained proximate a calibration element, the clamp member engaging the catheter tube to retain the end portion in desired proximity to a calibration element. Thus, the end portion is retained where desired and no mechanical apparatus need be actuated for positioning purposes prior to calibration.

The calibration element has optical properties suitable for use in calibrating a catheter through which light is propagated. It defines an open end cavity that has a size and shape adapted to receive the end portion of the catheter tube, and calibration proceeds with the end portion retained in this position.

The clamp member is in the form of a body of resiliently deformable material with which to hold the catheter tube and thereby retain the end portion in the cavity, and a retainer member retains the clamp member in generally fixed proximity with the open end of the cavity.

A channel-defining portion of the body of resiliently deformable material defines a longitudinally-opening channel generally aligned with the cavity axis, the channel having a size and shape adapted to receive the catheter tube coaxially in an interference fit. The catheter tube is received by movement into the channel radially after the end portion of the catheter tube has been placed into the cavity, and it inhibits movement of the catheter tube axially to thereby inhibit movement of the end portion within the cavity.

Thus, the device of this invention overcomes many drawbacks of the prior art. The catheter tube can be conveniently pressed into the clamp member for packaging, and peeled out for use. With the catheter tube engaged within the clamp member channel, the end portion may be packaged whereby it is retained securely in position proximate the calibration element so that nothing need be actuated to properly position the end portion for calibration purposes.

In addition, the device is mechanically less complicated and correspondingly less expensive, while still enabling convenient, repeatable catheter calibration. Moreover, the device is well adapted to mounting in a sterile catheter packaging tray to facilitate calibration prior to use. Thus, the clamp enables calibration of a catheter in a packaging tray without having to actuate any positioning mechanism.

Viewed from a different perspective, the catheter, or other form of light guide, is retained in the desired proximity with the calibration element using holding means with a generally longitudinally-opening slot. The slot enables more convenient insertion of the light guide into and removal from the holding means.

The above mentioned and other objects and features of this invention and the manner of attaining them will become apparent, and the invention itself will be best understood, by reference to the following description taken in conjunction with the accompanying illustrative drawings.

BRIEF DESCRIPTION OF THE DRAWINGS

FIG. 2 is a rear end view of the device taken on line 2—2 of FIG. 1;

FIG. 4 is an axially exploded assembly view of the device showing axial alignment of the various components and the catheter tube; and FIG. 5 is a cross sectional view taken on line 5—5 of FIG. 4.

DESCRIPTION OF THE PREFERRED EMBODIMENTS

Figure 1:
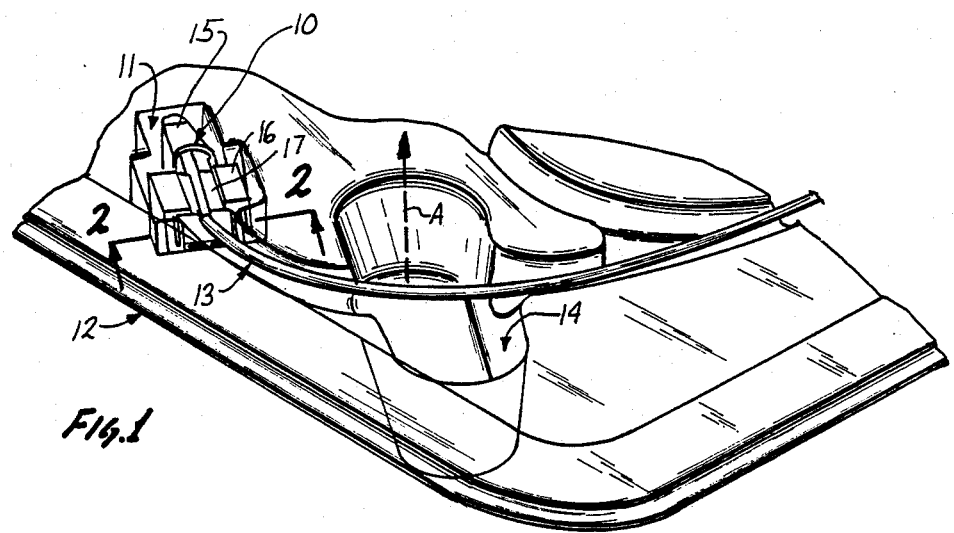
FIG. 1 of the drawings is an isometric view of a portion of a sterile packaging tray in which is disposed a catheter and a catheter calibration device constructed according to the invention.

Referring now to the drawings, and particularly to FIG. 1, there is shown a catheter calibration device 10 constructed in accordance with the invention. The device 10 is mounted in a recess 11 in sterile packaging tray 12 where it retains a catheter 13 pre-positioned in a desired calibration position. Once calibration is completed, the surgeon grasps the catheter 13 at the finger well 14 and lifts it as indicated by the arrow A in a direction generally normal to the tray 12, thereby dislodging the catheter 13 from the device 10 for use.

Although the device 10 is shaped and dimensioned for use with tray 12, the inventive concepts are equally applicable to any of many other shapes and sizes that the elements to be described may take. Generally, these elements include a calibration element 15, a retainer member 16, and a clamp member 17 that combine to achieve the improved attributes desired.

Considering first the calibration element 15 (FIGS. 2-5), it is fabricated according to known techniques, such as injection molding, using a suitable material such as a polyethylene material. It includes a forward portion 18 that is properly pigmented and covered by an attached light-blocking cap 18A to exhibit optical characteristics similar to those of a predetermined type of sample to be examined, such as blood, and it is intended for use with a light guiding catheter, such as the catheter 13.

More specifically, the calibration element 15 preferably has light-scattering, absorption, and reflection properties, which, in the aggregate (but not necessarily individually), are similar to those of a predetermined type of sample to be examined, such as blood. In order to provide the calibration element with the desired light-scattering properties, the calibration element 15 is pigmented in the sense that it includes a plurality of light-scattering particles distributed in a matrix.

The catheter 13 (FIGS. 1, 3, and 4) is a conventional type of catheter, such as an optical oxymetry catheter, and it includes a catheter tube 13A that extends past a balloon portion 13B of the catheter tube 13A to an end portion 13C that terminates in a face 13D. In a broad sense, the catheter tube 13A constitutes a light guide, and light propagated through the light guide or catheter tube 13A for calibration purposes passes out the face 13D (FIG. 3) and impinges upon the inner surface 19 of the calibration element 15. A major portion of the light penetrates the inner surface 19, and the light is scattered and reflected so that a portion returns back through the catheter tube 13A for measurement by suitable instrumentation connected to a proximal end of the catheter 13 (not shown). These measurements are used to characterize or calibrate the catheter and optical system, thereby enabling quantification of measurements to be taken of the sample.

The end portion 13C is preferably prepositioned in close proximity with the forward portion 18, and the calibration element 15 of the device 10 furthers this purpose. The illustrated forward portion 18 of the calibration element 15 includes an annular portion 20 (FIGS. 3 and 5) in which the end portion 13C of catheter 13 seats. This maintains the face 13D spaced slightly a known amount from inner surface 19 to facilitate positioning of the face 13D without contacting the inner surface 19.

In addition, the annular portion 20 defines a forward portion of the cavity having a size and shape that closely matches that of the end portion 13C, and may even provide an interference fit of the end portion 13D. This serves as light blocking means for inhibiting passage of light into the cavity beyond the end portion 13C. With an interference fit, it also serves as end portion engaging means for engaging the end portion 13C, thus contributing to retention of the end portion 13C within the cavity 23 in desired proximity with the inner surface 19.

Although the illustrated forward portion 18 results in a calibration position providing a slight space between the face 13D and inner surface 19, and although the forward portion 18 may provide for an interference fit, the forward portion 18 may be configured to omit either of these features without departing from the inventive concepts disclosed.

The forward portion 18 extends to a hood portion 21 of the calibration element 15 that combines with the forward portion 18 to define a cavity 23 (FIGS. 2-5) having a size and shape adapted to receive the end portion 13C of the catheter tube 13A. The cavity 23 extends along a cavity axis 24 (FIGS. 3 and 5) to a rearward portion 25 of the hood portion 21 that defines an open end or opening 26 of the cavity 23. The end portion 13C is inserted through the opening 26 into the cavity 23 to position it for calibration.

A conically-shaped intermediate portion 27 of the hood portion 21 disposed toward the forward portion 18 (FIGS. 3-5) flares outwardly away from the cavity axis 24 toward the opened end 26 to serve as shielding means for providing a shield that inhibits damage to the balloon portion 13B of the catheter tube 13A. An upwardly flared portion 29 of the hood portion 21 (FIGS. 2, 4, and 5) flares upwardly away from the cavity axis toward the opening 26 at a greater rate than it does laterally, and this provides an entranceway facilitating insertion of the end portion 13C of the catheter 13 into the cavity 23 before placing the catheter into the clamp member 17.

Considering next the retaining member 16, it is formed integrally with the calibration element 15 in the illustrated device 10, although it may be fabricated separately and attached by suitable means such as bonding. In another form of the invention (not shown) the packaging tray is configured to serve the retainer member function.

Figure 3:
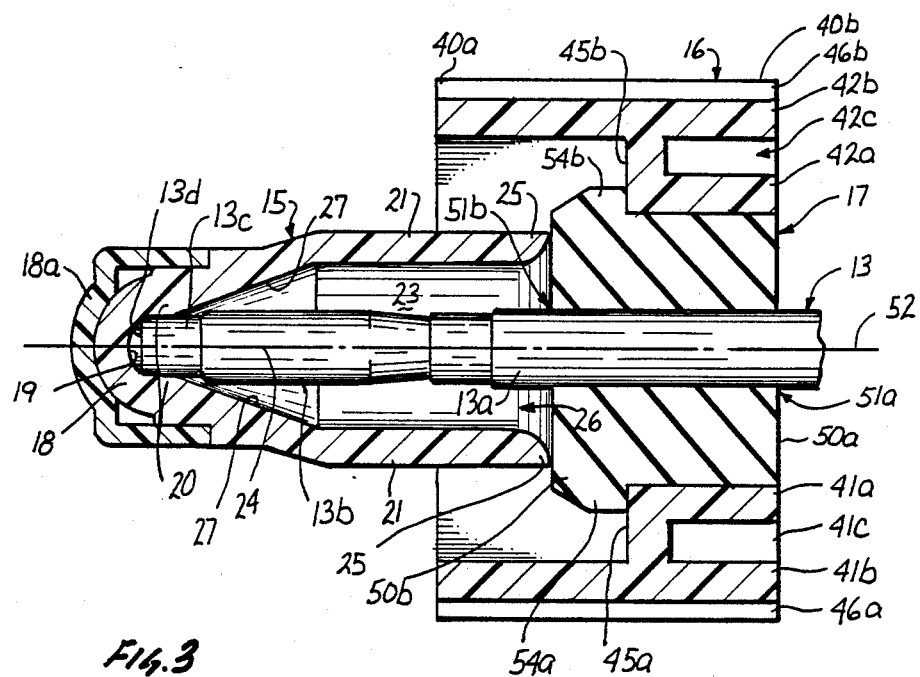
FIG. 3 is a cross sectional view of the device taken on line 3—3 of FIG. 2.

The retaining member 16 defines a compartment 40 having a size and shape adapted to receive the clamp member 17 snugly, and it serves the function of retaining the clamp member in proximity with the open end 26 of the cavity 23 as illustrated in FIGS. 3 and 5. The compartment 40 extends from a forward portion 40A (FIGS. 3-5) that defines an opening facing the opening 26 of the cavity 23 to a rearward portion 40B that defines a rearward opening through which to insert the clamp member 17 into the compartment 40. The retaining member 16 also includes an upward portion 40C (FIGS. 4 and 5) that defines an upward opening facilitating placement of the end portion 13C of the catheter tube 13A into the cavity 23 prior to pressing the catheter tube 13A into the clamp member 17 as will be subsequently described.

The retaining member 16 includes a left inner wall 41A and a left outer wall 41B separated by a space 41C. The space 41C is introduced according to known molding techniques as a molding expedient enhancing wall strength while reducing the amount of material employed to maintain consistent wall thickness. Similarly, the retaining member 16 includes an oppositely disposed right inner wall 42A and a right outer wall 42B separated by a space 42C.

A lower interior wall 43A and a lower exterior wall 43B separated by a pair of spaces 43C combine with the right and left walls and a pair of inwardly extending portions 44A and 44B to define the generally rectangular compartment cross section. The inwardly extending portions 44A and 44B are spaced apart a distance greater than the diameter of the catheter tube 13A to facilitate insertion of the catheter tube into the clamp member 17.

Disposed intermediate the forward portion 40A and the rearward portion 40B of the retaining member 16, oppositely disposed shoulders 45A and 45B (FIG. 3) serve to engage the clamp member 17 when it is inserted into the compartment 40. The shoulders 45A and 45B are spaced apart from the rearward portion 25 of the calibration element 15 appropriately to retain the clamp member 17 against the calibration element 15, the calibration element serving as a stop. In another embodiment (not shown), the retaining member includes a stop-defining portion that limits travel of the clamp member into the compartment, instead of having the clamp member abut the rearward portion of the calibration element.

Protruding portions 46A and 46B extending along the left and right exterior walls 41B and 42B (FIGS. 2-4) serve as packaging tray engagement means for retaining the device 10 on the tray 12. They have a size and shape adapted to snap into a pair of recessed portions 12A and 12B of the tray 12 for this purpose (FIG. 2). The device 10 is mounted on the tray 12 by inserting it into recess 11 until the protruding portions 46A and 46B snap into the recessed portions 12A and 12B, and when this is done the device 10 is retained on the tray 12 in a position wherein the catheter tube 13A can be moved generally perpendicular to an upper surface of the tray 12 and the cavity axis 24 for removal purposes.

The clamp member 17 is composed of a suitable resiliently deformable material, such as a silicone material liquid injected molded to the desired configuration according to known techniques. It includes an upper surface 50 extending between a rearward portion 50A and a forward portion 50B, and it includes a channel-defining portion 53 that defines a longitudinally-opening slot or channel 51 extending along a channel axis 52 from a rearward opening 51A defined by the rearward portion 50A to a forward channel opening 51B defined by the forward portion 50B of the clamp member 17.

The channel 51 has a circularly-shaped cross section in a plane generally perpendicular to the channel axis 52, and the channel is shaped and dimensioned so that it is slightly smaller than the cross section of the catheter tube 13A. This results in an interference fit of the catheter tube 13A within the channel 51. Thus, the clamp member 17 deforms slightly when the catheter tube 13A is pressed into the channel 51, and it grips the catheter tube 13A resiliently to retain the catheter tube in place.

The channel-defining portion 53 serves as catheter engaging means for receiving the catheter tube by movement of the catheter tube into the channel 51 radially, i.e., along a path having a component generally perpendicular to the channel axis 52. This is done after the end portion of the catheter tube has been placed into the cavity 23. The channel-defining portion 53 also inhibits movement of the catheter tube 13 axially after placement into the channel 51, i.e., along the channel axis 52, which in turn inhibits movement of the end portion 13C within the cavity 23.

The channel-defining portion 53 is part of the material of which the clamp member 17 is composed, and it defines a channel cross sectional area providing an interference fit of the catheter tube 13A within the channel. The cross sectional area thus defined extends generally in an arc greater than 180 degrees, an arc of approximately 270 degrees being defined by the illustrated channel-defining portion 53.

Although this is accomplished in the illustrated embodiment with a channel 51 having a generally uniform cross sectional area throughout its length, other channel cross sections may be employed to accomplish this function. In addition, the channel need not have a circularly-shaped cross section. Other channel configurations may be employed that serve the catheter tube engaging function, such as a plurality of inwardly-extending, circumferentially disposed ribs spaced apart along the channel.

The silicone material of which the illustrated clamp member 17 is composed exhibits a relatively high coefficient of friction with respect to the exterior of a conventional catheter tube, and this enhances frictional engagement of the catheter tube 13A by the clamp member 17. This significantly inhibits movement of the catheter tube 13A axially, i.e., along the channel axis 52, while enabling movement radially, i.e., along a path having a component generally perpendicular to the channel axis 52. Thus, the end portion 13C of the catheter 13 is held securely in desired proximity with the forward portion 18 of the calibration element 15.

The clamp member 17 includes a pair of outwardly extending or protruding portions or ears 54A and 54B. These mate with the shoulders 45A and 45B respectively of the retaining member 16 so that when the clamp member 17 is placed in the compartment 40 the ears 54A and 54B snap into engagement with the shoulders 45A and 45B. This restrains the clamp member 17 within the compartment 40 so that it does not move rearwardly out of the compartment 40. The clamp member 17 is thus retained in the compartment 40 where it is disposed in a position such that the channel axis 52 is generally aligned with the cavity axis 24.

Longitudinally-extending recesses 56A and 56B (FIGS. 2 and 4) serve as relief means for facilitating slight deformation of the clamp member 17 so that the channel 51 can be slightly enlarged during placement of the catheter tube 13A into the channel 51. Recess 56A is disposed between protrusions 55A and 55C, and recess 56B is disposed between protrusions 55B and 55D. These protrusions bear against the inner walls 41A and 42A so that the recesses 56A and 56B are slightly spaced apart from the inner walls 41A and 42A. This provides a degree of relief that better enables clamp member deformation, and protrusions can be provided on the inner walls instead of, or in conjunction with, protrusions on the clamp member to accomplish this function.

Rounded portions 57A and 57B (FIGS. 2 and 4) of the clamp member 17 serve as channel lead-in means for providing a lead-in to the channel 51 that facilitates placement of the catheter tube 13A into the channel 51 by movement generally perpendicular to the channel axis.

In operation, the device 10 is mounted in the recess 11 of packaging tray 12 by snapping the protrusions 46A and 46B into the tray recesses 12A and 12B. With the device 10 in this position, the end portion 13C of the catheter tube 13A is placed through open end 26 of the calibration element 15 into the cavity 23. The end portion 13C is then advanced to the forward portion 18 of the calibration element, to a position such that the face 13D is in desired proximity with the inner surface 19.

With the end portion 13C of the catheter tube 13A in desired proximity with the forward portion 18 of the calibration element 15, the catheter tube 13A is pressed passed the rounded portions 57A and 57B of the clamp member 17 into the channel 51, the clamp member 17 deforming resiliently as this is done. This seats the catheter tube 13A coaxially within the channel 51, with the channel-defining portion 53 engaging the catheter tube 13A to inhibit movement along the channel axis and thereby retain the end portion 13C in desired proximity with the calibration element 15.

Calibration is then accomplished when desired, usually just prior to use of the catheter 13, by interconnecting the catheter to suitable instrumentation for this purpose. Since the end portion 13C is prepositioned in a calibration position, i.e., held securely in desired proximity with the calibration element 15, further positioning or actuation of a mechanical positioning device is not required. A suitable cover on the tray 12 (not shown) retains the catheter 13 in a sterile condition as calibration proceeds so that the gloved surgeon need not be involved in the calibration procedure.

After calibration has been completed the catheter 13 is used by removing the cover from the tray, grasping the catheter tube 13A by placing the fingers in the finger well 14, and then lifting the catheter tube 13A so that the catheter tube is removed from the channel 51 in a direction generally perpendicular to the channel axis 52. The end portion 13C is then withdrawn from the cavity 23 to separate the catheter 13 from the calibration element for use. The device 10 is left in the tray 12 and these are discarded.

Thus, this invention provides a new and improved catheter calibration device with the desired attributes—one less complicated, less expensive, and less failure prone that achieves the desired function of catheter tube retention proximate the calibration element in a sterile environment enabling convenient, repeatable catheter calibration.

Although an exemplary embodiment of the invention has been shown and described, many changes, modifications, and substitutions may be made by one having ordinary skill in the art without necessarily departing from the spirit and scope of this invention.

What is claimed is:

1. A calibration device, comprising:
   a calibration element to be used in calibrating a separate catheter of the type having a catheter tube through which light can be propagated to an end portion of the catheter tube, the calibration element defining a cavity extending along a cavity axis to an open end that has a size and shape adapted to receive the end portion of the catheter tube for calibration purposes;
   a forward portion of the calibration element disposed opposite the opening in the cavity defining a forward portion of the cavity having a cross sectional area perpendicular to the cavity axis that closely matches the shape of the cross sectional area of the end portion of the catheter tube, serving as light blocking means for inhibiting passage of light into that portion of the cavity proximal to the end portion of the catheter tube;
   a body of resiliently deformable material with which the hold the catheter tube and thereby retain the end portion in the cavity;
   means for retaining the body of resiliently deformable material in generally fixed proximity with the open end of the cavity; and
   catheter tube engaging means, including a channel-defining portion of the body of resiliently deformable material defining a longitudinally-opening channel generally aligned with the cavity axis that has a size and shape adapted to receive the catheter tube coaxially in an interference fit, for receiving the catheter tube by movement of the catheter tube into the channel radially after the end portion of the catheter tube has been placed into the cavity, and for inhibiting movement of the catheter tube axially after placement into the channel to thereby inhibit movement of the end portion within the cavity.

2. A device as recited in claim 1, wherein the calibration element includes:
   end portion engaging means for engaging the end portion of the catheter tube within the cavity to further inhibit movement of the end portion within the cavity.

3. A device as recited in claim 2, wherein the end portion engaging means includes:
   a forward portion of the calibration element disposed opposite the opening in the cavity that defines a forward portion of the cavity having a size and shape adapted to provide an interference fit of the end portion of the catheter tube in the forward portion of the cavity.

4. A device as recited in claim 1, wherein the calibration element includes:
   shielding means for inhibiting damage to a catheter balloon portion of the catheter.

5. A device as recited in claim 4, wherein the shielding means includes:
   a flared portion of the calibration element disposed between the open end of the cavity and a forward portion of the calibration element disposed opposite the open end of the cavity, the flared portion flaring outwardly away from the cavity axis toward the open end of the cavity.

6. A device as recited in claim 1, wherein the calibration element includes:
   an upwardly flared portion that flares upwardly away from the cavity axis toward the open end of the cavity to provide an entranceway facilitating insertion of the end portion of the catheter tube into the cavity before placing the catheter tube into the channel.

7. A device as recited in claim 1, wherein the channel-defining portion includes:
   a portion of the body of resiliently deformable material defining a channel cross sectional area that extends generally in an arc greater than 180 degrees.

8. A device as recited in claim 7, wherein:
   the channel-defining portion includes a portion of the body of resiliently deformable material defining a channel cross sectional area that extends generally in an arc of approximately 270 degrees.

9. A device as recited in claim 1, wherein:
   the channel-defining portion defines a channel cross sectional area that is generally uniform throughout the length of the channel.

10. A device as recited in claim 1, wherein:
    the body of resiliently deformable material is in the form of a block of the resiliently deformable material having an upper surface in which the channel is disposed; and the block includes channel lead-in means defining a rounded portion of the block disposed between the upper surface and the channel for facilitating placement of the catheter tube into the channel.

11. A device as recited in claim 1, wherein:
the body of resiliently deformable material is composed of a material which frictionally engages the material of which the catheter tube exterior is composed.

12. A device as recited in claim 11, wherein:
the body of resiliently deformable material is composed of a silicone material.

13. A device as recited in claim 1, wherein the means for retaining the body of resiliently deformable material includes:
a retainer member attached to the calibration element, the retainer element having a size and shape adapted to receive the body of resiliently deformable material engagingly.

14. A device as recited in claim 13, wherein:
the retaining member defines a compartment in which to retain the body of resiliently deformable material, the retaining member having a forward portion defining a forward opening in the compartment facing the opening in the cavity, a rearward portion defining a rearward opening in the compartment through which to insert the body of resiliently deformable material into the compartment, and an upward portion defining an upward opening in the compartment through which to place the catheter tube into the channel.

15. A device as recited in claim 14, wherein:
the retaining member includes a pair of oppositely disposed shoulders in the forward portion of the retaining member to be used in retaining the body of resiliently deformable material within the compartment; and
the body of resiliently deformable material includes a pair of oppositely disposed protruding portions extending outwardly in a position disposed to engage the shoulders.

16. A device as recited in claim 15, wherein the body of resiliently deformable material includes:
relief means for maintaining a portion of the body of resiliently deformable material spaced apart from the retainer member to facilitate slight deformation of the body of resiliently deformable material as the catheter is placed into the channel.

17. A device as recited in claim 13, wherein:
the retainer member is integrally attached to the calibration element.

18. A device as recited in claim 17, wherein:
the calibration element and retainer member are composed of an injection molded polyethylene material.

19. A device as recited in claim 13, wherein the retainer member includes:
packaging tray engagement means, including a protruding portion of the retainer member having a size and shape adapted to mate with a recessed portion of a separate packaging trap in which the calibration device is to be packed, for retaining the calibration device on the packaging tray.

20. A device as recited in claim 19, wherein:
the protruding portion is adapted to retain the calibration device on the packaging tray in a position wherein the catheter tube can be removed from the channel by movement generally perpendicular to an upper surface of the tray.

21. A calibration reference apparatus for use with a light guide having an end portion which terminates in an end face, comprising:
a calibration element defining a cavity, said cavity extending along a cavity axis to an opening at one end and otherwise being essentially optically closed, said opening being sized to receive the end portion of the light guide in the cavity with the end face of the light guide confronting an inner surface of the cavity opposite said opening whereby the light guide can direct light from the end face thereof across a gap between the end face of the light guide and said opposite surface, and against said opposite surface;
said calibration element being adapted to return at least some of the light which is directed into the gap from the end face of the light guide;
a forward portion of the calibration element disposed opposite the opening in the cavity defining a forward portion of the cavity having a cross sectional area perpendicular to the cavity axis that closely matches the shape of the cross sectional area of the end portion of the light guide, serving as light blocking means for inhibiting passage of light into that portion of the cavity proximal to the end portion of the light guide;
means coupled to said calibration element for releasably holding the light guide in the cavity; and
said holding means comprising, a body of resiliently deformable material with which to hold the light guide and thereby retain the end portion in the cavity, means for retaining the body of resiliently deformable material in generally fixed proximity with the open end of the cavity, and light guide engaging means, including a channel-defining portion of the body of resiliently deformable material defining a longitudinally-opening channel generally aligned with the cavity axis that has a size and shape adapted to receive the light guide coaxially in an interference fit, for receiving the light guide by movement of the light guide into the channel radially after the end portion of the light guide has been placed into the cavity, and for inhibiting movement of the light guide axially after placement into the channel to thereby inhibit movement of the end portion within the cavity.

22. An apparatus, comprising:
a packaging tray;
an optical catheter in said packaging tray, said optical catheter having an end portion and a distal face of said end portion;
an optical calibration element in said packaging tray, said optical calibration element defining a cavity extending along a cavity axis to an open end that has a size and shape adapted to receive the end portion of the optical catheter for calibration purposes;
a forward portion of the calibration element disposed opposite the opening in the cavity defining a forward portion of the cavity having a cross sectional area perpendicular to the cavity axis that closely matches the shape of the cross sectional area of the end portion of the optical catheter, serving as light blocking means for inhibiting passage of light into that portion of the cavity proximal to the end portion of the optical catheter;

means for holding the optical calibration element in said packaging tray in a substantially fixed position; and means for releasably retaining the optical catheter in the packaging tray with the distal end face in a calibration position without having to actuate the releasable retaining means from the exterior of the packaging tray;

said releasable retaining means comprising a body of resiliently deformable material with which to hold the optical catheter and thereby retain the end portion in the cavity of the optical calibration element, means for retaining the body of resiliently deformable material in generally fixed proximity with the open end of the cavity, and optical catheter engaging means, including a channel-defining portion of the body of resiliently deformable material defining a longitudinally-opening channel generally aligned with the cavity axis that has a size and shape adapted to receive the optical catheter coaxially in an interference fit, for receiving the optical catheter by movement of the optical catheter into the channel radially after the end portion of the optical catheter has been placed into the cavity, and for inhibiting movement of the optical catheter axially after placement into the channel to thereby inhibit movement of the end portion within the cavity.

23. An apparatus as recited in claim 22, wherein the packaging tray includes:

a recessed portion of the packaging tray defining a recess having a size and shape adapted to receive a calibration device engagingly.

24. An apparatus as recited in claim 22, wherein the packaging tray includes:

a portion of the packaging tray defining a finger well to facilitate grasping of the catheter tube with the fingers of a user for catheter removal purposes.

25. An apparatus, comprising:

a packaging tray;

an optical calibration element mounted on the packaging tray;

means for holding the optical calibration element on the packaging tray in a substantially fixed position;

an optical catheter on said packaging tray, said optical catheter having a distal end face;

means for releasably retaining the optical catheter on the packaging tray with the distal end face in a calibration position in which the optical catheter can be calibrated using the optical calibration element; and said retaining means including means responsive to a force on said catheter in a direction generally transverse to the catheter at said retaining means for releasing the catheter from the retaining means.

26. An apparatus as recited in claim 25, wherein the packaging tray includes:

a, portion of the packaging tray defining a finger well to facilitate grasping of the catheter tube with the fingers of a user for catheter removal purposes.

* * * * *